United States Patent [19]
Mansour

[11] Patent Number: 6,057,165
[45] Date of Patent: *May 2, 2000

[54] QUALITY CONTROL PROCEDURE FOR MEMBRANE FLOW-THROUGH DIAGNOSTIC ASSAY DEVICES

[75] Inventor: James David Mansour, Pleasanton, Calif.

[73] Assignee: Becton, Dickinson and Company, Franklin Lakes, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/798,396

[22] Filed: Feb. 7, 1997

[51] Int. Cl.$^7$ .................................................. G01N 33/543
[52] U.S. Cl. .............................. 436/518; 422/56; 422/57; 422/58; 422/99
[58] Field of Search .............................. 436/518; 422/58, 422/56, 57, 99; 607/153

[56] References Cited

U.S. PATENT DOCUMENTS

| | | | |
|---|---|---|---|
| 4,508,821 | 4/1985 | Mansour et al. | 435/34 |
| 4,622,298 | 11/1986 | Mansour et al. | 435/34 |
| 4,665,024 | 5/1987 | Mansour et al. | 435/34 |
| 4,693,834 | 9/1987 | Hossom | 210/767 |
| 4,797,259 | 1/1989 | Matkovich et al. | 422/101 |
| 4,900,633 | 2/1990 | Gillery | 428/432 |
| 4,912,030 | 3/1990 | Weiss et al. | 435/5 |
| 4,912,034 | 3/1990 | Kalra et al. | 422/56 |
| 4,916,056 | 4/1990 | Brown, III et al. | 435/7 |
| 4,920,046 | 4/1990 | McFarland et al. | 435/7 |
| 4,962,023 | 10/1990 | Todd et al. | 435/7 |
| 4,978,625 | 12/1990 | Wagner et al. | 436/518 |
| 5,006,464 | 4/1991 | Chu et al. | 435/7.1 |
| 5,008,080 | 4/1991 | Brown, III et al. | 422/56 |
| 5,073,340 | 12/1991 | Covington et al. | 422/56 |
| 5,132,085 | 7/1992 | Pelanek | 422/55 |
| 5,185,127 | 2/1993 | Vonk | 422/56 |
| 5,204,061 | 4/1993 | Covington et al. | 422/56 |
| 5,240,844 | 8/1993 | Wie et al. | 435/7.92 |
| 5,260,025 | 11/1993 | Covington et al. | 422/56 |
| 5,268,146 | 12/1993 | Lawrence et al. | 422/57 |
| 5,354,692 | 10/1994 | Yang et al. | 436/514 |
| 5,516,644 | 5/1996 | Yamauchi et al. | 435/7.9 |
| 5,541,057 | 7/1996 | Bogart et al. | 435/5 |
| 5,547,833 | 8/1996 | Dorval et al. | 435/5 |
| 5,567,627 | 10/1996 | Lehnen | 436/518 |
| 5,627,041 | 5/1997 | Shartle | 435/7.24 |
| 5,639,428 | 6/1997 | Cottingham | 422/112 |
| 5,725,831 | 3/1998 | Reichler et al. | 422/56 |
| 5,753,519 | 5/1998 | Durst et al. | 436/518 |
| 5,783,148 | 7/1998 | Cottingham et al. | 422/56 |

OTHER PUBLICATIONS

Clark, Brian R. et al, 1987, Chapter 8, pp. 167–179 Emzyme–immuno assay, CRC Press.

Primary Examiner—James C. Housel
Assistant Examiner—Ginny Allen Portner
Attorney, Agent, or Firm—Bruce S. Weintraub

[57] ABSTRACT

The present invention relates to a flow-through device that has a quality control procedure for a binder used in the test area of an assay device to bind an analyte from a test sample. The invention provides for a method for determining the presence of an analyte in a fluid sample, said method employing an assay test kit including an assay device having a porous membrane having an upper surface and a lower surface, a test area on the upper surface of said membrane, a binder for the analyte attached to said test area; a delivery device comprising a well for receiving the sample, said well having an opening at a lower end thereof, wherein said sample is capable of being delivered through the well to a portion of the test area on the upper surface of said porous membrane of the assay device; a vessel containing a tracer having a tag, wherein said tracer is for application to said portion of the test area whereby the tag of said tracer is detected in said portion of the test area when the analyte is present in the fluid sample; and a vessel containing an analyte positive control sample comprising said analyte which is applied to the test area and said tracer is applied to the test area whereby the tag of said tracer is detected in said test area thus confirming that said analyte is specifically bound by said binder in the test area.

16 Claims, 8 Drawing Sheets

QUALITY CONTROL PROCEDURE FOR MEMBRANE FLOW-THROUGH DIAGNOSTIC ASSAY DEVICES

FIELD OF THE INVENTION

This invention relates to a class of diagnostic assay devices known as flow-through assay devices used to detect the presence of an analyte. In particular, this invention relates to a flow-through assay device that has a quality control procedure for a binder used in a test area of an assay device to specifically bind an analyte from a test sample. The invention also relates to assay kits which use the flow-through assay device.

BACKGROUND OF THE INVENTION

Assays for determining analytes by a solid phase technique involve contact between a sample suspected of containing the analyte and a device having a binder material specific for the analyte supported on a porous membrane. The amount of analyte which becomes bound to the binder on the porous membrane is then detected with a tracer as a measure (quantitative or qualitative) of the analyte in the sample.

Many companies have introduced assay test kits to screen for Group A Streptococcus ("GAS") in the physician's office. Other companies have introduced assay kits for home use to detect pregnancy and kits to detect ovulation. Some of these assay kits are enzyme immunoassays where the formation of a colored species indicates the presence (or absence) of the analyte.

Other assay kits presently available are agglutination immunoassays, typically using latex or erythrocytes as supports. Many assays do not give a clear indication of assay test results and lead to questions about the reliability of the test results. Furthermore, in the case of agglutination assays, test results are difficult to read at low analyte concentrations and suffer sometimes from non-specific agglutination.

A problem with current assay device technology is the lack of built-in quality control testing in an assay device for the binding material used to specifically bind an analyte of interest. Normally, in order to confirm that the binding material in the assay device used in the test was operational for a particular analyte, repeat testing utilizing a control sample of the analyte is required. The control test in many cases is carried out on another device from the same batch of assay devices used for the original assay. This results in customer dissatisfaction due to the increased cost of using an additional assay device for quality control testing. Furthermore, since the control test is not performed on the assay device used in the original assay, it is not a direct binder control test for the assay device used in the original test, but rather one for the binder in a batch of test devices.

Efforts have been made to develop assays which incorporated controls into assay devices in order to confirm the operativeness of the assay device. A test card incorporating a calorimetric indicator to determine the presence of a minute amount of a specific substance in a liquid medium was disclosed in U.S. Pat. Nos. 5,240,844 and 4,900,633 both to Wie et al. The test card has a test area which incorporates a binding support (e.g. a bacterial binding substrate) having a dense application of antibodies for the particular substance being tested. The test card also incorporates a control area which is juxtaposed to the test area, the control area incorporates the same binding support and antibody as the test area.

The assay disclosed by Wie et al. consists of administering a sample of a specific substance, i.e. an antigen, being tested in a liquid medium to the test port of the device. Any antigen present in the sample will immediately become bound to the antibodies immobilized on the binding support. The next step is the application of an aqueous solution of enzyme labelled antigen at the test port which will bind to any available antibodies. The next step involves the administration of a solution which will displace the solution containing uncombined, enzyme labelled antigen in the test port. If all of the antibodies in the test port were saturated with antigen from the test substance then no color indication will be observed because no enzyme-linked antigen was able to bind to the antibodies in the test port. However, if no antigens were present in the test substance, complete color saturation will be observed.

In the control port the enzyme-labelled antigens will completely saturate the antibodies and thus full color development will result, indicating both the operativeness of the device and the maximum color definition which can be expected if no antigens are present in the test substance.

Another device with a control region was disclosed in U.S. Pat. No. 4,916,056 to Brown et al. The device is useful in solid phase binding assays to determine the presence or amount of an analyte in a test sample. A positive control area is formed by providing a substance such as the analyte of interest which is capable of binding the enzyme label or other signal response material within the device control area. The positive control area and the analyte binding area are preferably in an interactive configuration in which the positive control area interacts with the analyte binding area upon the occurrence of a positive test result to form a first representational symbol having a known meaning to the user, and the positive control area acts alone upon the occurrence of a negative test. The positive control area disclosed by Brown et al. is used to indicate the operativeness of the enzyme label or other signal response material used to indicate the presence of an analyte rather than the operativeness of the reagent used in the test area to bind a particular analyte of interest.

U.S. Pat. No. 5,073,340 to Covington et al. discloses a test device for use in determining analyte wherein a binder for an analyte (e.g., antibody) to be detected is supported on a porous membrane. The use of an analyte positive control or negative control is disclosed. The control area may be completely or partially overlapping with the test area or it may be a completely separate area of the support. The analyte control disclosed by Covington indicates to the user that the tracer used to detect the presence of the desired analyte in the device was active.

U.S. Pat. No. 5,132,085 to Pelanek discloses an assay device having a frame with three wells at the bottom of which there is a reaction surface comprising an appropriate membrane, the membrane is in turn in contact with a liquid-absorbing material underneath. Antibody-carrying beads are attached to the reaction surface in each of the wells. One well serves the function of a control well. When a test sample is run on the assay the antibody on the beads complexes with its antigen (if present), which in turn complexes with a conjugate antibody bearing an appropriate label, that is added later. In the control well, beads are deposited that can serve as negative and positive controls. The deposited control beads have the antibody-antigen complex, which insures that when a viable labeled conjugate reagent is properly added as part of the procedure that the positive control area should display a detectable symbol. Accordingly, Pelanek's quality control procedure is for the labeled conjugate reagent and not for the antibody used in the assay.

Assay devices to date that have built-in control tests are directed to the operativeness of the labeling material used to indicate the presence of a desired analyte. A need has existed for a flow-through assay device having a built-in control test in the assay device that indicates the operativeness of the binding material used in the assay to specifically bind an analyte in a test sample. Additionally, it is also desirable that such an assay device also incorporate a control test for any labeled material used to indicate the presence of an analyte in such an assay. The present invention fulfills these needs.

SUMMARY OF THE INVENTION

This invention relates to a method for determining the presence of an analyte in a fluid sample, said method employing an assay test kit including an assay device having a porous membrane having an upper surface and a lower surface, a test area on the upper surface of said membrane, a binder for the analyte attached to said test area; a delivery device comprising a well for receiving the sample, said well having an opening at a lower end thereof, wherein said sample is capable of being delivered through the well to a portion of the test area on the upper surface of said porous membrane of the assay device; a vessel containing a tracer having a tag, wherein said tracer is for application to said portion of the test area whereby the tag of said tracer is detected in said portion of the test area when the analyte is present in the fluid sample; and a vessel containing an analyte positive control sample comprising said analyte which is applied to the test area and said tracer is applied to the test area whereby the tag of said tracer is detected in said test area thus confirming that said analyte is specifically bound by said binder in the test area; said method comprising:

- contacting the portion of the test area of the assay device using the delivery device with the fluid sample and the tracer having a tag that is visible when bound at the portion of the test area under assay conditions such that any analyte and tracer not specifically bound at the portion of the test area flows through the test area;
- removing the delivery device and determining visibility of the tag of the tracer specifically bound at the portion of the test area as a measure of analyte present in the fluid sample;
- contacting the test area of the assay device with the analyte positive control sample and the tracer having a tag that is visible when bound at the test area under assay conditions such that any analyte and tracer not specifically bound at the test area flows through the test area; and
- determining visibility of the tag of the tracer specifically bound at the test area as an indication that said analyte is specifically bound by said binder in the test area of the assay device.

DETAILED DESCRIPTION OF THE INVENTION

Figure 1:
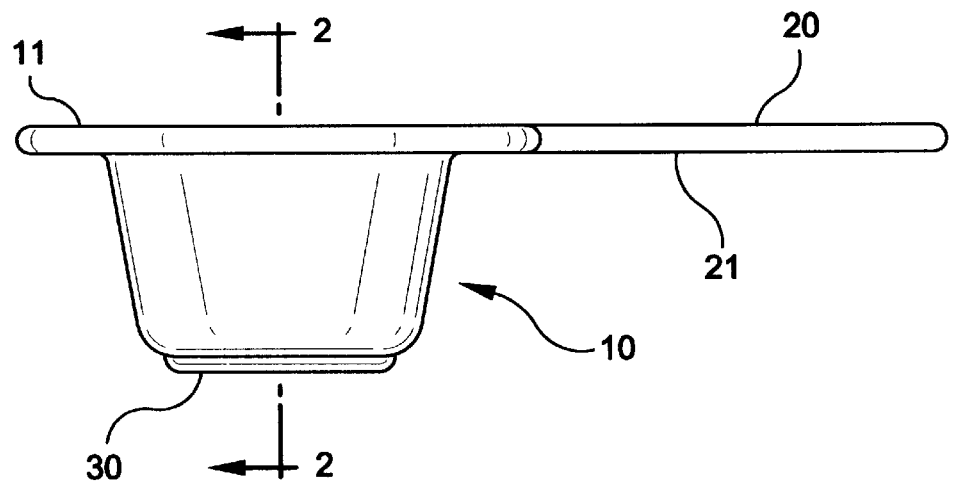
FIG. 1 is a side elevational view of one embodiment of the delivery device of the present invention.

The present invention provides for an assay device having an assay composite comprising one or more membranes. One membrane present in the assay composite is a porous membrane with a test area containing a specific or non-specific binder for an analyte of interest. The assay device also provides for an analyte positive control test area, a portion of which or none of which may overlap with the test area used in the assay. An assay for a desired analyte is performed on the test area of the assay composite followed by a quality control test in the designated analyte positive control area to confirm that the binder in the test area specifically bound the analyte of interest.

An analyte may be determined (qualitatively or quantitatively) by applying a sample suspected of containing the analyte and a tracer having a tag, either a particulate label or an enzyme label, to a portion of the test area using a delivery device having a well with an opening at the bottom. Alternatively, the tracer with the tag may be added using the delivery device to the portion of the test area after the test sample. Depending on the chemistry of the assay, reactions take place and presence or absence of a detectable signal from the tag of the tracer is indicative of the presence of the analyte.

Preferred embodiments of the assay and delivery devices of the present invention may be constructed as described in commonly assigned European Pat. No. 0 334 015 B1, which is hereby incorporated by reference. In order to determine that the binder used in the test area of the assay device specifically bound the analyte of interest an analyte positive control test is performed in its designated analyte positive control area. The analyte positive control test comprises running an analyte positive control sample (i.e. either a solution or suspension of the desired analyte) through the binder in the analyte positive control area of the assay device. The tracer having the tag used to detect the presence of the analyte in the test sample is used to detect the presence of the analyte positive control sample on the binder and may be added either with the analyte positive control sample or at a later time. The analyte positive control sample and the tracer having a tag may be provided or not. If the binding material is capable of binding the analyte positive control sample then the tag of the tracer in the test area will be detected.

A preferred assay composite includes a porous membrane for supporting the binder at the test area in a concentration whereby the tracer used in the assay, when bound to the test area, under assay conditions is visible without further treatment. The term "visible" as used herein means that the material can be detected with the naked eye without the use of instrumentation; although instrumentation may be used to detect the intensity of the absorbance or fluorescence of the material.

The assay composite may optionally include a flow control layer having an upper and lower surface with the upper surface of the flow control layer adjacent to the lower surface of the porous membrane. The flow control layer may be formed of a porous material having a pore size to control the rate of flow of assay reagents through the test area. The assay composite may also preferably include a porous spacer layer having an upper and a lower surface, for spacing an absorbent layer having an upper and lower surface, formed of an absorbent material, from the flow control layer. A preferred assay composite also includes an absorbent layer which is a porous material having an absorbing or absorbent capacity sufficient to absorb the liquids which flow into the test area during the assay. The absorbent layer also functions to provide a driving force (e.g., a concentration differential) which causes reagents applied to the test area of the assay device to flow into the absorbent layer.

The entire porous membrane may be formed of the material used as the binder in the test area. Alternatively, only the binder in the test area may be formed of such a material.

In addition, since the assay composite is employed in a manner such that the assay reagents flow through its layers, the porous membrane has a pore size which is greater than the size of the particulate label employed in the assay so that portions of the tracer, which do not become bound under assay conditions, flow into the absorbent layer and are not visible at the test area. In general, the porous membrane should have a pore size which is at least 2 μm, and most preferably at least 5 μm. In general, the pore size does not exceed 12 μm. It is to be understood, however, that although the previously described pore sizes are preferred, other pore sizes may be employed, depending upon the materials used in the assay.

In the case where a flow control layer is used in the assay composite, the porous material employed in forming the flow control layer has a pore size which is less than the pore size of the material employed for forming the porous membrane. Thus, in effect, the flow control layer functions to reduce the rate of flow of assay reagents through the more porous test area. The pore size of the flow control layer, as well as the thickness of the flow control layer, is preferably controlled in a manner such that the flow of assay reagents through the test area provides the requisite sensitivity as well as a rapid and accurate assay.

In accordance with one particularly preferred embodiment, the layer for controlling the rate of flow through the assay composite is dimensioned and sized in a manner such that the flow rate of materials through the test area is in the order of at least 0.5 ml/min, and generally no more than 2 ml/min.

The flow control layer is preferably formed from a non-fibrous material such as polycarbonate and has pores or channels of a uniform size that provide for unidirectional flow from the test layer to the layer beneath the flow control layer. Immediately below the flow control layer of the preferred assay composite, a spacer layer is provided. It is a porous material which functions as a spacer between the flow control layer and the absorbent layer. The porous spacer layer has a pore size greater than the pore size of the flow controlling layer so that the spacer layer does not function to restrict flow through the assay composite.

The materials which are employed in forming the various layers of the assay composite are selected to have the characteristics described above. In addition, such materials should not produce non-specific binding of analyte or tracer. The materials may inherently have such characteristics, or alternatively, the materials may be treated to prevent non-specific binding; for example, treatment with an appropriate protein, such as bovine serum albumin. The porous membrane of the assay composite is preferably also treated with a wetting agent in order to insure proper flow of the assay reagents through the test layer and into the absorbent layer. Representative examples of wetting agents include sucrose, glycerol, glucose, and sorbitol. The porous membrane may be simultaneously treated with a protein and wetting agent (e.g., an aqueous solution of bovine serum albumin and sucrose).

In general, the assay composite is mounted on or in a suitable holder, such as a card or a container to form an assay device. The preferred assay composite is provided with a cover having an aperture covering the test area. Alternatively, the assay composite may be covered with a card including an aperture which overlies the test area whereby the liquid sample and various assay reagents are applied directly to a portion of the test area through a delivery device.

The selection of a suitable holder for the assay composite is deemed to be within the scope of those skilled in the art.

The delivery device of the present invention delivers fluid samples to a portion of the test area of the in vitro diagnostic assay device. It is comprised of a well for receiving a fluid sample, an opening in the bottom of the well and may also have a flow controlling membrane covering the opening. The size and shape of the opening and the mean pore size of the flow controlling membrane are selected so that a fluid in the well is delivered to a top surface of an assay composite.

The delivery device is constructed with the well and the opening in the bottom of the well being sized and shaped to mate with a test area of an assay device. With this construction the delivery device serves to deliver fluids across a portion of the surface of the test area.

In one preferred embodiment, the opening at the bottom of the well of the delivery device is covered by a flow control membrane. The flow controlling membrane may be attached to the bottom of the well of the delivery device using a variety of techniques, for example, heat-sealing, sonic-welding, gluing, or the membrane may be press-fitted between the bottom of the delivery device and a ring holder on the outside of the delivery device. In one preferred embodiment the flow control membrane has a mean pore size of 3 microns or 1.2 microns (Immunodyne™ Cat. Nos. B1A030HC5 and B1A012HC5 respectively, Pall Corporation, East Hills, N.Y.). The opening at the bottom of the delivery device well may have any shape desired. Typical shapes include a square, a circle, a triangle, a rectangle or any other shape desired.

In another aspect of the invention the delivery device serves a further function of removing interfering substances from fluids to be used in the assay. This function may be accomplished by coating the interior walls of the well, the flow control membrane or both with a specific binding species that binds the interfering substance without binding the analyte and species active in the assay. Preferably, the flow control membrane is coated with a specific binding species. For example when the assay uses antibodies from mice, rabbits, or goats and very low levels of analyte are to be detected, antibodies present in a patient's sera to the animal species used to make the reagents can cause false positive results. This problem may also exists when monoclonal antibodies are used.

In yet another aspect of the invention the flow controlling membrane of the delivery device when present may have reagents for the assay releasably coated on it. This allows dry storage of the reagents prior to use. Then as the sample and other fluids are passed through the flow controlling membrane, the reagents are eluted to the assay device.

A most preferred construction of the delivery device further comprises a handle secured to the well. The handle allows handling of the device without touching any fluids that have been placed in the well.

In accordance with the present invention, a binder which is to be applied to a test area of a porous membrane, preferably as an aqueous solution or suspension is optionally mixed with a detectable marker, which is preferably a chromogen, and in particular a fluorescent material. The mixture of binder and detectable marker is then applied to a defined test area of the porous membrane, such as, for example, a spot, square, circle, triangle, or any other shape desired, in a manner to support both the binder and the detectable marker in the test area. While those skilled in the art are familiar with a variety of coupling techniques to securely attach a binder to a porous membrane, adsorption is preferred. The procedure for adsorbing the binder can be any of those commonly available for pattern coating of materials including gravure printing, silk screening and other conventional printing methods.

The porous membrane which is used is one which has a surface area (area/unit weight of material) such that the binder can be supported on the porous membrane in a concentration (weight/unit area) such that under assay conditions, a tag of a tracer used to determine the presence of an analyte is visible without further treatment.

The porous membrane may be formed from, but is not limited to, the following materials: nitrocellulose, nylon, glass fiber, cellulose acetate, polysulfone and teflon, having a surface area sufficient to support the binder in a concentration as described above.

The porous membrane is preferably formed from a cellulose ester with nitrocellulose giving exceptionally good results. The term "nitrocellulose" refers to nitric acid esters of cellulose, which may be nitrocellulose alone, or a mixed ester of nitric acid and other acids, and in particular, aliphatic carboxylic acids having from one to seven carbon atoms, with acetic acid being preferred. Sheets which are formed from cellulose esterified with nitric acid alone, or a mixture of nitric acid and another acid such as acetic acid, are often referred to as nitrocellulose paper.

The binder supported on the porous membrane is preferably present in at least one microgram per $cm^2$, most generally at least 10 micrograms per $cm^2$, and preferably 40 micrograms per $cm^2$. The residual binding capacity of the porous membrane may be saturated or blocked by treatment of the porous membrane with one or more types of proteins which do not specifically bind materials to be employed in the assay. Thus, for example, residual binding capacity may be blocked by use of bovine serum albumin. A wetting agent, such as a detergent, may also be applied to the porous membrane.

In some cases, in applying the binder (in particular an antibody) to the porous membrane, a polyhydroxy compound (e.g., glycerol, erythritol, and sorbitol), or a sugar (e.g., glucose and sucrose) is included in the antibody solution to prevent non-specific binding (false positives) during the assay.

In the case where a detectable marker is used with the binder, the preferred materials for use are fluorescent materials which do not adversely affect the binding ability of the binder, and which are capable of being adsorbed by the porous membrane. As representative examples of suitable fluorescent materials, there may be mentioned Acridine Orange, Pyronin Y, Texas Red, Rhodamine 6, with such materials being employed in amounts which do not adversely affect the binding ability of the binder, which are detectable when subjected to ultraviolet light, and which are not detectable with the naked eye. If the material used as a detectable marker includes groups which may be reactive with the binder or the analyte positive control, such groups may be blocked prior to admixing the material, for example they may be placed in a buffer including a source of amino groups (e.g. glycine) that react with reactive sites on the detectable marker and thereby prevent further reactivity which could influence the biological activity of the binder or provide sites for non-specific binding under assay conditions.

After the binder has been supported on the porous membrane, the test area may be distinguished from the background area by detecting the detectable marker. Thus, for example, in the case where the detectable marker is a fluorescent material, the membrane may be exposed to excitation energy of a suitable wave length (e.g. ultraviolet light from conventional U.V. lamps). The detectable marker will emit a characteristic fluorescent signal which is preferably detectable with the naked eye.

The tracer is comprised of a specific ligand portion and a tag, where the ligand portion is one member of a specific binding pair (such as an antigen and complimentary antibody) and the tag consists of an enzyme label or a particulate label (solid or solid-like, as opposed to non-solid labels, such as radioisotopes, and various fluorescent materials). The particulate label is visible under the assay conditions so that the presence or amount of analyte may be determined without further treatment and without the use of instrumentation; e.g., by the use of a liposome containing a colored material as the particulate label.

In the preferred assay chemistry, if the assay is in a competitive format, the ligand portion of the tracer would be one which is bound by the binder supported on the porous membrane. If the assay is in a sandwich format, then the ligand portion of the tracer would be bound by the analyte. Such assay formats and amplification procedures are generally known in the art, and a further description is not required for a complete understanding of the present invention.

If the tag is detectable by color (as in colormetric enzyme tags and direct detection with a colored material) the color should be observable in the presence of the detectable marker. Presently preferred are colored particulate labels, such as liposomes including a chromogen, colloidal metals or dyed latex. The selection of a suitable tag is deemed to be within the scope of those skilled in the art.

In the assay technique, the tracer having a tag is applied to at least the portion of the test area used in the assay, and in the case where an analyte positive control sample is used, the tracer having a tag is also applied to at least the analyte positive control area.

As indicated above, in producing the preferred tracer the ligand portion is labeled with either a particulate label or an enzyme label. Particulate labels can be but are not limited to sacs, such as liposomes, colloidal metals, polymer microcapsules and polymer latex particles. To be useful, the particulate label also includes a colored substance, either internal to the particle or on its surface, and such that when used in the assay for the analyte, the tracer is visible without the need to use instrumentation, or without the destruction of the sac to release the colored substance.

A sac which is used to label the ligand portion of the tracer may be any one of a wide variety of sacs, including but not limited to liposomes (single walled or multilamellar) or polymer microcapsules (for example, those made by coacervation, or interfacial polymerization).

Polymer microcapsules also may be produced by procedures known in the art except that the solution in which the microcapsules are formed also includes the tag whereby the interior of the polymer microcapsule encompasses the tag. The preparation of such microcapsules is disclosed for example in Mircroencapsulation Processes and Applications, edited by Jan E. Vandegger (Plenum Press, 1974).

As known in the art, liposomes can be prepared from a wide variety of lipids, including phospholipids, glycolipids, steroids, relatively long chain alkyl esters; e.g., alkyl phosphates, fatty acid esters; e.g., leitchin, fatty amines and the like. A mixture of fatty materials may be employed, such as a combination of a neutral steroid, a charged amphiphile and a phospholipid. As illustrative examples of phospholipids, there may be mentioned lecithin, sphingomyelin, dipalmitoyl, and the like. As representative steroids, there may be mentioned cholesterol, cholestanol, lanesterol, and the like. As representative examples of charged amphiphilic compounds, which generally contain from 12 to 30 carbon atoms, there may be mentioned mono- or dialkyl phosphate ester or an alkylamine; e.g., diacetyl phosphate, stearyl amine, hexadecyl amine, dilauryl phosphate, and the like.

The liposome sacs are prepared in an aqueous solution including the tag whereby the sacs will include the tag in their interior. The liposome sacs may be prepared by vigorous agitation in the solution, followed by removal of tag from the exterior of the sac. Further details with respect to the preparation of liposomes are set forth in U.S. Pat. No. 4,342,826 and PCT International Publication No. WO 80/01515, both of which are hereby incorporated by reference.

The tracer may also be produced by labeling the ligand portion with an aqueous dispersion of a hydrophobic dye or pigment, or a polymer nucleus coated with such a dye or pigment. Such labels are described in more detail in U.S. Pat. No. 4,373,932, which is hereby incorporated by reference. The tracers produced in accordance with that patent may also be employed as tracers in the present invention.

The visible particulate label may be visible polymer particles, such as colored polystyrene particles, preferably of spherical shape.

Representative examples of other suitable particulate labels include ferritin, phycoerythrins or other phycobiliproteins; precipitated or insoluble metals or alloys; fungal, algal, or bacterial pigments or derivatives such as bacterial chlorophylls; plant materials or derivatives, and the like.

The ligand portion of the tracer may be labeled with the particulate label so as to produce a tracer for use in the invention by procedures generally known in the art, with the procedure which is used being dependent upon the choice of ligand portion and the particulate label. Such techniques include covalent coupling, derivatization or activation, and the like. In producing a tracer wherein the ligand is labeled with a sac, the sac may be produced from a component which has been derivatized with a ligand portion, whereby the sac, when produced, is coupled to the ligand portion.

In one preferred embodiment the binder used in the assay device may be applied to the porous membrane in admixture with a fluorescent material having a characteristic emission band within the visible spectrum and observable as a first color (such as yellow), and an analyte positive control sample may be applied in admixture with a fluorescent material having a characteristic emission band within the visible spectrum and observable as a second color (such as red), which is distinguishable from the first color. After application of both the analyte positive control sample and the binder, the porous membrane may be exposed to excitation energy of suitable wavelengths to detect the presence of both colors to thereby determine the presence, in their respective areas, of both the binder and the analyte positive control. Preferably the excitation wavelengths for the detectable marker and the tag of the tracer are in the ultraviolet range of the spectrum and in the absence of U.V. irradiation, they are colorless or are colored with a relatively weak intensity.

While the chemistry of the assay is independent of the present invention, the preferred assay chemistry uses interactions among specific binding pairs to determine the presence of analyte. One preferred type of specific binding pair is an antigen/antibody pair.

In the method of the present invention a fluid sample is delivered to the well of the delivery device and allowed to flow out of the opening across the flow controlling membrane, if present, to a portion of the test area of the assay device. Thereafter reagents of a tracer system can be delivered to the test area through the delivery device or independently of the delivery device when performing the quality control procedure for the binder. Thus, where the flow rate of a tracer conjugate across the test area is important to control, the delivery device can be used to effect control. Similarly in some systems multiple delivery devices may be used to deliver species of dramatically different sizes at controlled rates.

Thus, in accordance with the preferred embodiment of the present invention, an assay employs a tracer wherein the tag portion of the tracer may be a visible label, and wherein the assay is performed on a test area of an assay composite, the assay composite is preferably formed from a plurality of layers of material having different characteristics, as described above, and wherein the assay reagents flow-through the layers of the assay composite.

The invention also provides for a kit comprising a delivery device and an in vitro diagnostic assay device, matched to its fluid delivery capabilities. Thus systems can be developed where the delivery device and a flow-through assay device are matched for a particular analyte and assay format.

Referring now to the drawings, the delivery device of the present invention is comprised of a well 10 having at its top outwardly extending flanges 11 and depending sidewalls 12. The depending sidewalls 12 end at a bottom 13. An opening 14 in the bottom 13 allows a fluid in the well to flow out. The delivery device preferably has a handle 20 secured to the well 10. The handle 20 preferably has a section 21 with a cross section thinner than the remainder of the handle to make the handle readily flexible.

The well and handle are conveniently integrally formed by molding. The choice of material is not critical. Persons skilled in the art are familiar with suitable plastics. The well should be large enough to hold a fluid sample, e.g. 400 $\mu$L. The opening is sized to achieve the flow rate desired for the assay in question. It can conveniently have a diameter in the range of 0.05 to 0.22 inches. Preferably the opening has a diameter of 0.12 inches.

If a flow-controlling membrane 30 is used, it is secured to the bottom of the well of the delivery device. Flow-controlling membranes are available from a variety of sources known to those skilled in the art. Presently preferred is a nylon 66 membrane having a mean pore size of 3.0 microns (Immunodyne™, Pall Corporation, East Hills, N.Y. 11548). The membrane can be secured to the well by any suitable method including with an adhesive by heat sealing and by ultrasonic welding.

Figure 3:
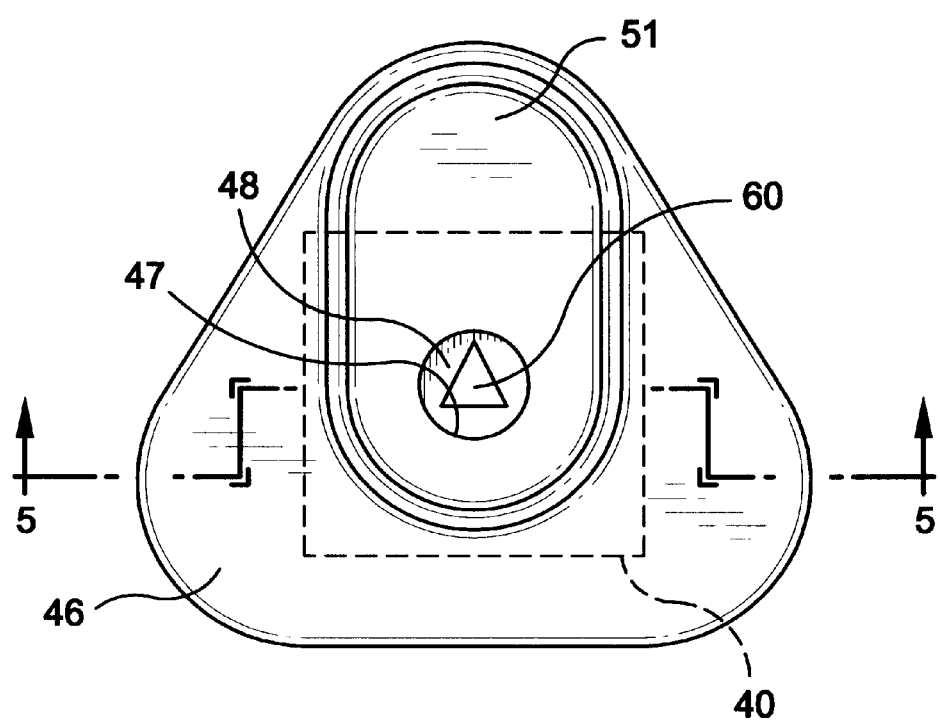
FIG. 3 is a top planar view of the preferred flow-through diagnostic assay device for use in the kit of the present invention.
Figure 4:
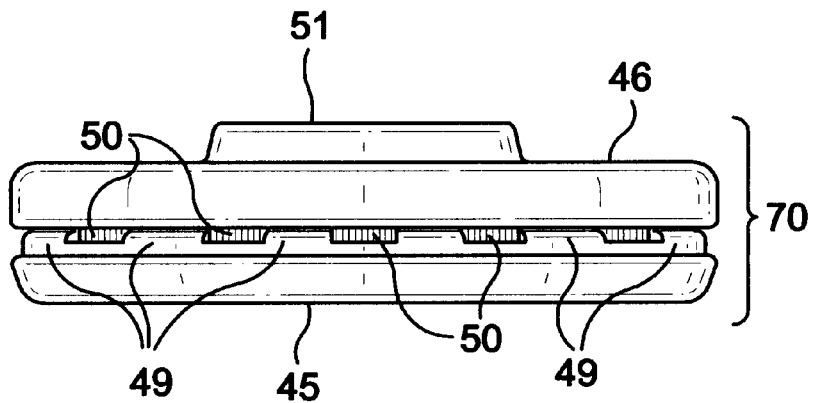
FIG. 4 is an elevational view of the assay device shown in FIG. 3.
Figure 5:
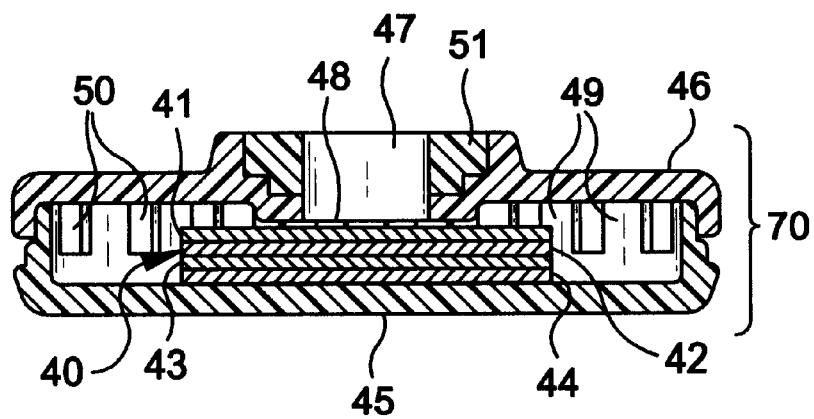
FIG. 5 is a sectional view of the flow-through assay device shown in FIG. 3 taken along section line 5—5.

The preferred kit of the present invention uses the delivery device described above and the flow-through diagnostic assay device shown in FIGS. 3–5. The assay composite 40 is comprised of a porous membrane 41 having upper and lower surfaces and a test area 48 on its upper surface formed by the application of a binder. A preferred material porous membrane is nitrocellulose, which has a pore size in excess of 2 $\mu$m, and generally less than 12 $\mu$m. More preferable is a pore size of about 3 $\mu$m to 5 $\mu$m. Most preferable is a pore size of 5 $\mu$m. Adjacent to the lower surface of the porous membrane 41 is a flow control layer 42 which is preferably formed from a unidirectional flow-controlling polycarbonate membrane having a pore size of 0.6 micron.

Immediately underneath the flow control layer 42 is a porous spacer layer 43 which generally has a pore size greater than the pore size of flow controlling layer 42. The layer 43 may be formed, for example, from a non-woven polyacetate. Immediately underneath the porous spacer layer 43 is absorptive layer 44. The absorbent layer 44 is preferably formed from a cellulose material, e.g., absorbent cellulose paper. Thus, the assay composite is comprised of layers 41, 42, 43 and 44, which are preferably combined to produce a unified assay composite 40. The layers may be attached to each other, for example, by sewing of the layers to each other; however, other methods of attachment are possible.

The assembled assay composite is conveniently placed within a container comprised of base 45 and cover 46 to form an assay device 70. In a preferred embodiment the base and cover of the assay device have three sides in a generally triangular shape with rounded corners. The cover 46 which overlies porous membrane 41 includes a raised portion having a suitable aperture 47 which overlies the test area 48. As shown in FIG. 3, within test area 48 the triangular region 60 represents the portion of the test area which is covered when a delivery device 10 is inserted into the aperture of the assay device. The test area outside of triangular region 60 is not exposed to a test sample during an assay but is used for quality control testing of the binder used in the test area of the assay device.

The cover 46 is supported over porous membrane 41 by teeth-like projections 49 extending upward from the sides of the base 45. The projections 49 are of sufficient height to provide air spaces 50 which provide for ventilation of the sides of the assay composite 40.

The raised portion of the cover 46 surrounding the aperture 47 may include a colored area 51, the color of which contrasts from that of cover 46 and the color to be generated in the test area provides for a better reading of the test results which are generally determined by color. In a preferred embodiment, the container comprised of base 45 and cover 46 having colored area 51 are made of plastic materials.

Preferably the delivery device is formed so that the wall 10 fits in the aperture 47 in the container top. Most preferably the bottom of the well is sized and shaped to mate with the bottom of the aperture 47 and the top of the well is sized and shaped to mate with the top of the aperture 47. In use the fluid sample and any reagents for which flow control is desired are added to the well of the delivery device 10 and allowed to flow through the membrane 30 to the test area 60. When the delivery device is no longer needed it can be removed by the handle and discarded.

The test area 60 of the assay device 70 is used to determine the presence of an analyte. A test sample is applied to the test area 60 through delivery device 10 whereby the sample contacts the binder in test area 60, with the sample flowing through the assay composite to the absorbent layer 44. The analyte present in the sample will become specifically bound to the binder in area 60.

Thereafter, tracer is applied to the test area 60 through the delivery device 10. The tracer becomes bound to the analyte, and any unbound portion flows through to the absorbent layer 44.

If desired, a wash solution may be applied to the test area 60 prior to addition of the tracer. Similarly, after addition of the tracer, a wash solution may be applied to the test area 60 to wash any tracer which may not be specifically bound to the complex in the test area 60, into the absorbent layer 44.

On removal of the delivery device 10 from the aperture 47, the presence of color in the test area 60 is indicative of the presence of analyte, and if the assay is to be a quantitative assay, the intensity of such color is indicative of the quantity of analyte present in the sample.

The quality control test to confirm that the binder in test area 60 specifically bound the analyte is carried out by adding an analyte positive control sample containing analyte to the test area 48 through the aperture 47 whereby the analyte positive control sample contacts all of the binder in the test area 48, with the sample flowing through to the absorbent layer 44. The analyte present in the sample will become bound to the binder in test area 48. Next a tracer is applied to the test area through the aperture 47 of the assay device 70. The tracer becomes bound to the analyte and the presence of color in the test area 48 is indicative of the operativeness of the binder for the analyte.

Figure 6A:
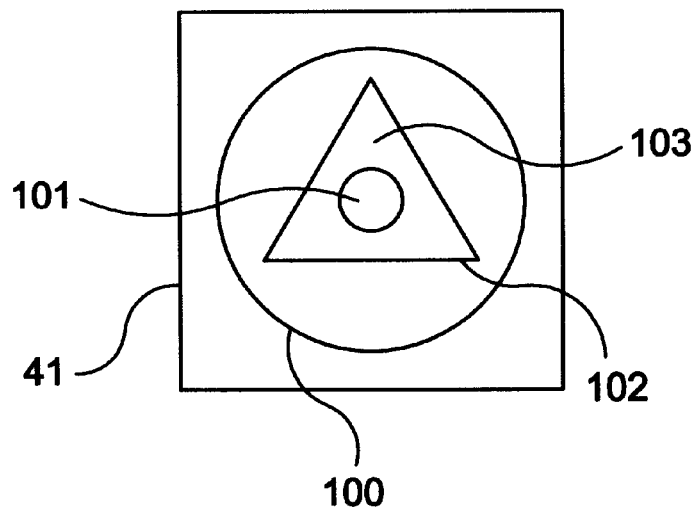
FIGS. 6A–6E are top views of the porous membrane of an assay device of the present invention, wherein the analyte positive control area and the test area overlap.
Figure 6B:
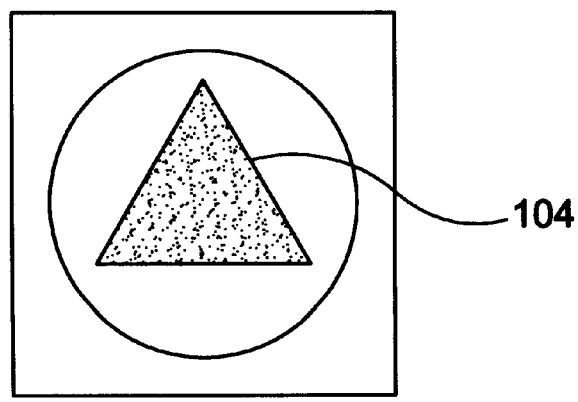
Figure 6C:
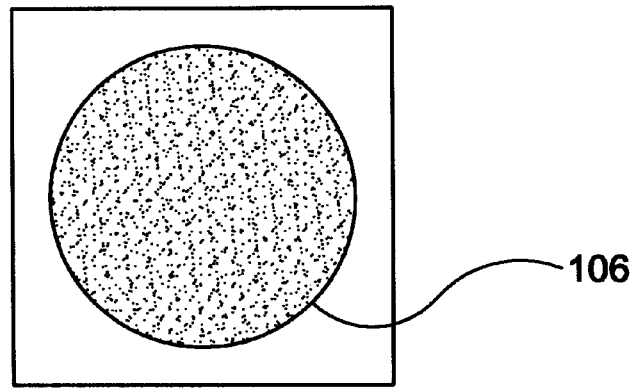
Figure 6D:
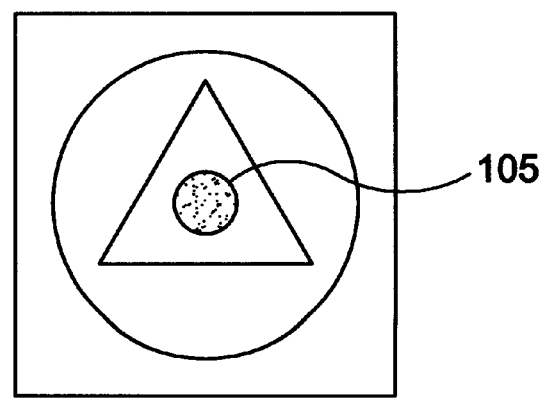

In a preferred embodiment of the invention a porous membrane 41 is shown in FIG. 6A which comprises a binder on the porous membrane surface. The binder may either detect analytes in a specific or non-specific manner. In the case of a binder that binds analytes in a specific manner an antibody 100 is spotted at the center of the porous membrane 41 to form a test area for an analyte of interest. The antibody 100 at the center of the device is further spotted with a small amount of the analyte of interest 101. A patient sample is run through a portion 103 of the antibody 100 at the test area using a delivery device. The delivery device has a triangular opening at the bottom of a well, the triangular opening is represented by the triangle 102. If the desired analyte is present in the sample, a colored triangular shape 104 will be present when the test area of the assay device is developed due to the formation of the analyte-antibody complex as shown in FIG. 6B. However, if no analyte is present in the patient sample a colored round spot 105 will be observed at the center of the assay device as shown in FIG. 6D. The colored round spot 105 is due to the analyte-antibody complex formed due to the analyte that was originally spotted on the antibody in FIG. 6A.

Figure 6E:
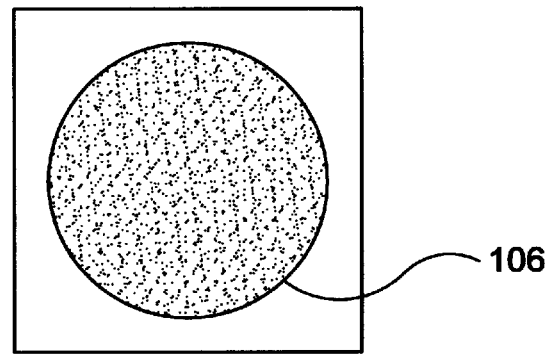

A quality control test is run on each of the used assay devices to confirm that the antibody specifically bound the analyte of interest. The quality control test is conducted by running an analyte positive control sample through all of the antibody 100 on the porous supports of each of the used assay devices. When the test areas of the used assay devices are developed the antibody on the porous membrane is completely colored 106 as shown in FIGS. 6C and 6E due to the formation of the analyte-antibody complex. Accordingly, the color of the test area's size and shape changes due to the quality control test making it easy for a user to conclude that the antibody specifically bound the desired analyte of interest.

Figure 7A:
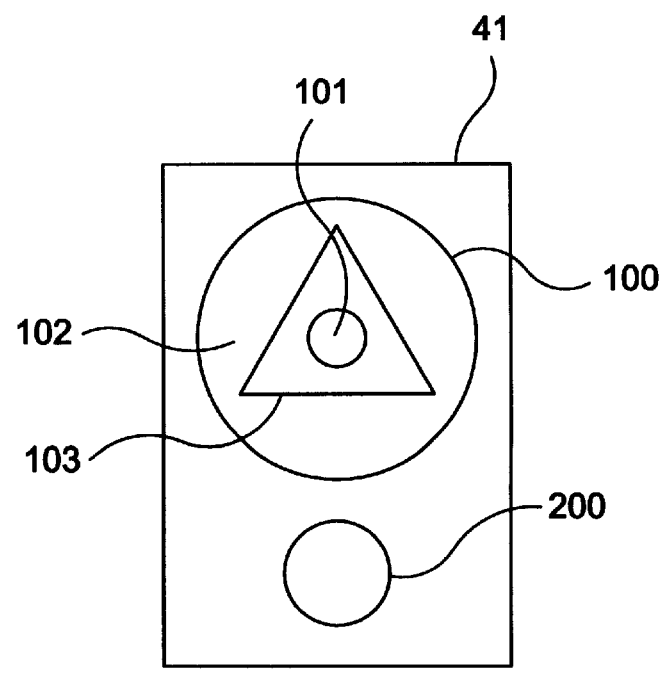
FIGS. 7A–7E are top views of the porous membrane of an assay device of the present invention, wherein an analyte positive control area is located on the bottom portion of the porous membrane.
Figure 7B:
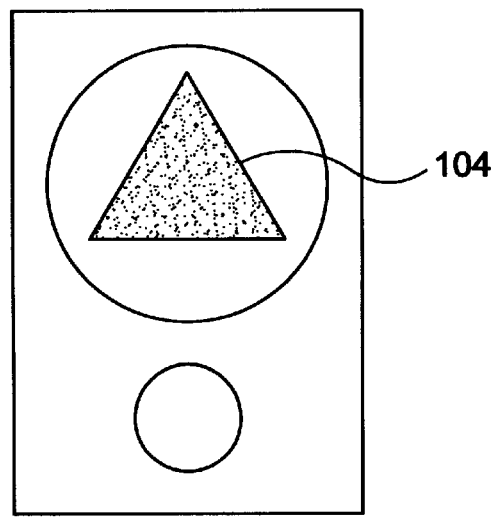
Figure 7C:
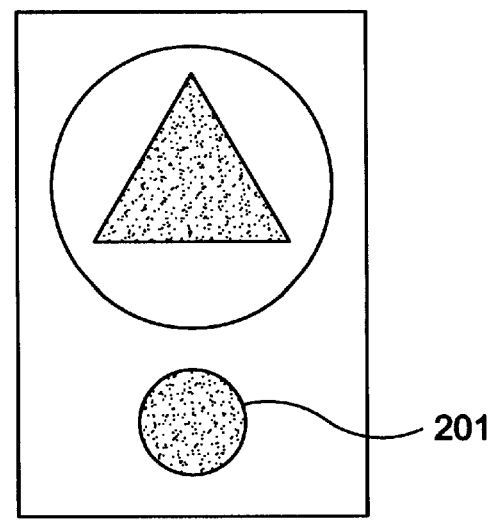
Figure 7D:
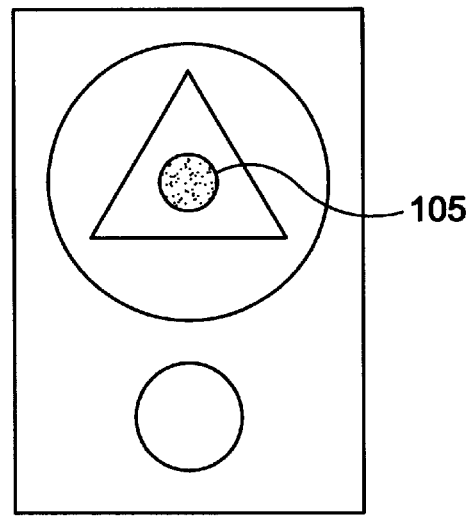
Figure 7E:
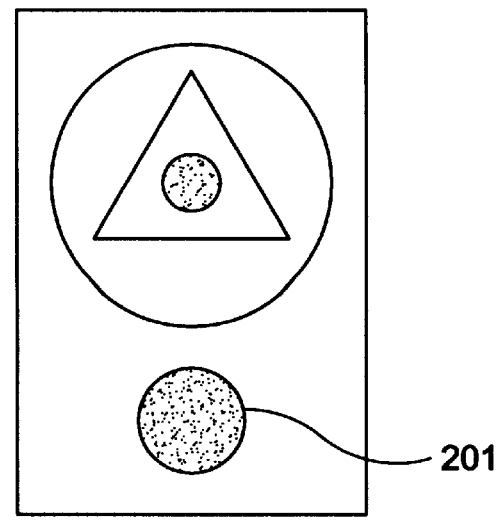

Analyte positive control testing may be performed on used assay devices having an analyte positive control area 200 outside of the test area as shown in FIG. 7A. The analyte positive control area 200 has antibody spotted as shown in FIG. 7A. If the assay results in either a positive or negative result, FIGS. 7B and 7D respectively, an analyte positive control sample is run through the analyte positive control area 200. If the antibody specifically bound the analyte of interest a colored circle 201 is observed in the analyte positive control area of the used assay devices, FIGS. 7C and 7E respectively.

The present invention is applicable to procedures and products for determining a wide variety of analytes. As representative examples of types of analytes, there may be mentioned; drugs, including therapeutic drugs and drugs of abuse; hormones, vitamins, proteins, including antibodies of all classes; peptides; steroids; bacteria; fungi; viruses; parasites; components or products of bacteria, fungi, viruses, or parasites; allergens of all types; and products or components of normal or malignant cells. As particular examples, there may be mentioned T4; T3; digoxin; hCG; insulin; theophylline; luteinizing hormone; organisms causing or associated with various disease states, such as Streptococcus Pyogenes (group A), Herpes Simplex I and II, cytomegalovirus, rubella, chlamydia, and Candida Albicans.

The analyte may be determined in various samples, including, for example, body fluids, such as saliva, urine, serum, and cerebral spinal fluid or from swab samples, e.g., from the throat.

Although the invention has been described with respect to a preferred embodiment as shown in the drawings, the present invention is equally applicable to depositing binder, and optionally also analyte positive control on a porous membrane other than the one particularly shown. Thus, the assay composite of the assay device may be in the form of a single layer or two layers, with a test area on top of the assay composite. Similarly, these and other modifications should be apparent to those skilled in the art.

This invention will be better understood from the Examples which follow. However, one skilled in the art will readily appreciate that the specific methods and results discussed are merely illustrative of the invention and no limitation of the invention is implied.

EXAMPLE 1

PREPARATION OF A TYPICAL DIAGNOSTIC ASSAY DEVICE

A porous support membrane such as nitrocellulose having an average pore size of 5 microns (MSI, Westborough Mass.) is coated with a polyclonal antibody or a monoclonal antibody in a buffer solution such as phosphate buffered saline. After drying, the membrane is blocked with protein (e.g. 0.5% gelatin in 0.1 M phosphate buffered saline, pH 8.0). After the membrane has dried a small area of the membrane bound antibody is allowed to react with antigen resulting in a small circular zone of antigen now bound to the antibody. The membrane is then dried. An assay composite is assembled by placing the porous membrane on top of a layered composite. The two bottom layers are absorbent cellulose pages (1¼ in square); above these bottom layers is a porous spacer layer comprised of a non-woven web of rayon (Schleicher and Schuell, Keane N. H., Cat. #5-S). Above the rayon layer is a polycarbonate unidirectional flow controlling membrane having a mean pore size of 1.0 micron (Nucleopore, Pleasantville, Calif.). Smaller pores cause liquids to flow slower into this composite, while larger pores allow faster flow. The four layers of the composite are attached together and the nitrocellulose porous membrane is placed on top. The assembled compact is approximately 10 square cm in area and 0.5 cm in thickness. This composite is placed in a container as shown in the FIGS. 1–5.

PREPARATION OF A DELIVERY DEVICE

Figure 2:
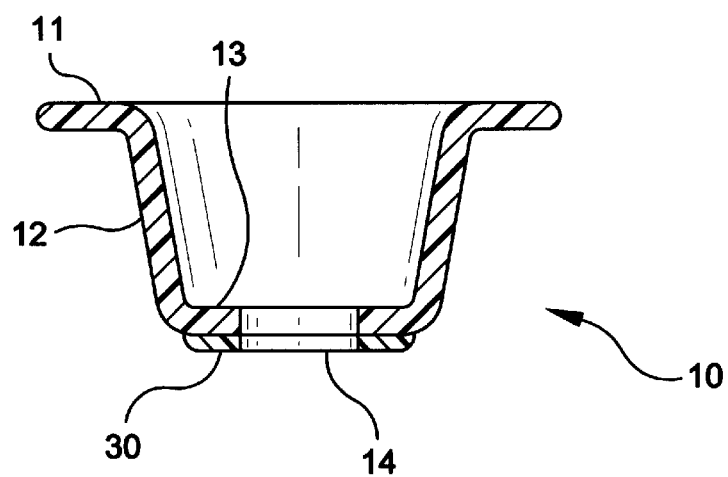
FIG. 2 is a cross section taken along section line 2—2 of FIG. 1.

A well and handle are molded from a plastic material. One preferred plastic material is polystyrene resin (K-resin KR03, Phillips Petroleum, Bartlesville, Okla.). The well is cylindrical in shape with an outside diameter of 0.395 inch. The capacity of the well is 400 $\mu$l. The wall is formed with a 0.12 inch triangular opening in its bottom as illustrated in FIGS. 1 and 2. The well fits snugly in the aperture of the flow-through assay device.

EXAMPLE 2

QUALITY CONTROL TEST FOR GROUP-A-STREPTOCOCCUS (GAS) ASSAY DEVICE

GAS assay devices were assembled as in Example 1. The IgG fraction of rabbit anti-GAS polyclonal antibody was used as the coating on nitrocellulose. It was applied to the membrane in the shape of an equilateral triangle by allowing 50 $\mu$l of antibody at 1.0 mg/mL concentration to pass through a triangular opening placed in contact with the nitrocellulose. GAS antigen, to be used on the device (as described in Example 1) as well as the liquid control was prepared by extraction of Group A Streptococci (approximately $1\times10^{10}$) with nitrous acid: 300 $\mu$l of 0.1 M HCl was mixed with 40 $\mu$l of 4 M NaNO$_2$ and allowed to react with the streptococci for 3 minutes. The extraction was terminated by the addition of 40 $\mu$l of 1 M Tris base (Trizma™, Sigma Chemical Company, St. Louis, Mo.).

Tracer for GAS devices was prepared as previously described in U.S. Pat. No. 4,920,046 (McFarland et al.), incorporated herein by reference: antigen affinity purified rabbit anti-GAS polyclonal antibody was covalently coupled to liposomes containing sulforhodamine B.

A quality control evaluation of GAS extracted antigen control was conducted to determine if a test device that has a negative result for the presence of GAS in a patient's sample will test positive when a GAS control is run on the device that indicated that no GAS was present in the patient's sample.

1. Five assay devices were run with negative GAS samples (Table 1, Device Nos. 1–5) followed by the addition of the tracer and then washed with guanidine HCL (1 M). A determination of the intensity of color on the test area was made by sight. Color intensity was evaluated on a scale of 0–4 with 0 representing no color and 4 representing very intense color. Sight evaluation of the color of the test area indicated that no GAS was present in the samples.

2. The five assay devices (Table 1, Device Nos. 1–5) which were used in step 1 were then re-tested with an extracted positive GAS sample followed by the addition of tracer and then washed with guanidine HCl (1 M). A determination of the intensity of color was made by sight. All devices yielded a high level of color (3.0) indicating the presence of the GAS in the sample tested, thus confirming that the antibody was active for the GAS antigen.

3. A control experiment was conducted on another five un-run assay devices (Table 1, Device Nos. 6–10) which were each tested with the positive GAS sample followed by the addition of the tracer. A determination by sight of the intensity of color that developed in the test area due to the tracer was made. Each of the test devices 6–10 indicated that the antibody was active for the GAS antigen.

TABLE 1

Assay result for GAS assay device numbers 1–10.

| Device No. | Color intensity of portion of test area assayed with GAS negative samples | Color intensity of complete test area following retesting with GAS positive samples | Device No. | Color intensity of complete test area following testing with GAS positive samples |
|---|---|---|---|---|
| 1 | 0 | 3.0 | 6 | 3.5 |
| 2 | 0 | 3.0 | 7 | 3.5 |
| 3 | 0 | 3.0 | 8 | 3.0 |
| 4 | 0 | 3.0 | 9 | 3.0 |
| 5 | 0 | 3.0 | 10 | 3.0 |

EXAMPLE 3

QUALITY CONTROL TEST FOR RSV (RESPIRATORY SYNCYTIAL VIRUS) ASSAY DEVICES

RSV assay devices and delivery devices were obtained as part of a kit from Becton Dickinson & Company, Hunt Valley, Md. (Directigen RSV, Cat. #8530-40). The assay devices are the same as those described in Example 1, except that a nylon membrane is used in place of nitrocellulose. In addition, no antibody coating is used as the RSV antigen binds to the membrane without the use of specific binding antibody.

RSV negative clinical specimens were delivered to a portion of the test area of five assay devices using the delivery device provided with the kit. The kit's tracer was then added to the portion of the test area contacted by the test sample through the delivery device. The test area was then washed with the kit's wash solution to develop the color on the test area. Next, a determination of the intensity of color on the test area was made by sight. Color intensity was evaluated on a scale of 0–4 with 0 representing no color and 4 representing very intense color. Sight evaluation of the color of the test area indicated that no RSV was present in the test samples. The devices were all scored as having no color (0).

The delivery device was removed from each assay device aperture and the devices were re-run with a positive antigen control from the Directigen kit. When the assays were developed all assay devices had an intense color which was consistent with a positive result.

What is claimed is:

1. A method for determining the presence of an analyte in a fluid sample, said method employing an assay test kit including an assay device having a porous membrane having an upper surface and a lower surface, a test area on the upper surface of said membrane, a binder for the analyte attached to said test area, a flow control layer having an upper and lower surface wherein the upper surface of the flow control layer is adjacent to the lower surface of the porous membrane, a porous spacer layer having an upper and lower surface wherein the upper surface of the porous spacer layer is adjacent to the lower surface of the flow control layer, and an absorptive layer having an upper and lower surface wherein the upper surface of the absorptive layer is adjacent to the lower surface of the porous spacer layer; a delivery device comprising a well for receiving the fluid sample, said well having an opening at a lower end thereof, wherein said fluid sample is capable of being delivered through the well to a portion of the test area on the upper surface of said porous membrane of the assay device; a vessel containing a tracer having a tag, wherein said tracer is for application to said portion of the test area whereby the tag of said tracer is detected in said portion of the test area when the analyte is present in the fluid sample; and a vessel containing an analyte positive control sample comprising said analyte which is applied to the test area and said tracer is applied to the test area whereby the tag of said tracer is detected in said test area thus confirming that said analyte is specifically bound by said binder in the test area; said method comprising:

(a) running the assay device by:
(i) contacting the portion of the test area of the assay device using the delivery device with the fluid sample and the tracer having a tag that is visible when bound at the portion of the test area under assay conditions such that any analyte and tracer not specifically bound at the portion of the test area flows through the test area;
(ii) removing the delivery device and determining visibility of the tag of the tracer specifically bound at the portion of the test area as a measure of analyte present in the fluid sample;

(b) re-running the assay device by:
(i) contacting the test area of the assay device with the analyte positive control sample and the tracer having a tag that is visible when bound at the test area under assay conditions such that any analyte and tracer not specifically bound at the test area flows through the test area; and
(ii) determining visibility of the tag of the tracer specifically bound at the test area as an indication that said analyte is specifically bound by said binder in the test area of the assay device.

2. The method of claim 1, wherein said assay device further comprises an analyte positive control area on the upper surface of said porous membrane.

3. The method of claim 2, wherein the porous membrane of the assay device is nitrocellulose.

4. The method of claim 3, wherein the nitrocellulose has a pore size of 3 $\mu$m to 5 $\mu$m.

5. The method of claim 1, wherein the binder is an antibody.

6. The method of claim 5, wherein a detectable marker is attached to the binder.

7. The method of claim 6, wherein the detectable marker is a chromogen.

8. The method of claim 7, wherein the chromogen is a fluorescent material.

9. The method of claim 7, wherein the detectable marker is detectable when illuminated by a suitable wavelength of light.

10. The method of claim 6, wherein the detectable marker is distinguishable from the tag of the tracer.

11. The method of claim 1, wherein the analyte is one member of a specific binding pair, the binder is the other member of the specific binding pair and the tracer specifically binds to the analyte at sites not interfering with the specific binding reaction between the analyte and the binder.

12. The method of claim 1, wherein the analyte and the tracer specifically bind to the binder.

13. The method of claim 1, wherein the well of the delivery device has a flow controlling membrane covering the opening.

14. The method of claim 1, wherein the tag of the tracer is an enzyme label or a particulate label.

15. The method of claim 1, wherein the fluid sample and the tracer are contacted simultaneously with the test area.

16. The method of claim 1, wherein the analyte positive control sample and the tracer are contacted simultaneously with the test area.

* * * * *